United States Patent [19]

Nova et al.

[11] Patent Number: 5,670,323

[45] Date of Patent: Sep. 23, 1997

[54] PROCESS FOR THE DETECTION OF MALIGNANT MELANOMA

[75] Inventors: Michael Philip Nova, La Jolla; Ana-Maria Gonzalez, Del Mar; Andrew Baird, San Diego, all of Calif.

[73] Assignee: The Whittier Institute for Diabetes and Endocrinology, La Jolla, Calif.

[21] Appl. No.: 459,296

[22] Filed: Jun. 2, 1995

Related U.S. Application Data

[63] Continuation of Ser. No. 900,646, Jun. 18, 1992, abandoned.

[51] Int. Cl.$^6$ .......................... C12Q 1/68; G01N 33/574
[52] U.S. Cl. .............................. 435/6; 435/7.1; 435/7.23
[58] Field of Search .............................. 435/6, 7.1, 7.23

[56] References Cited

FOREIGN PATENT DOCUMENTS

| | | |
|---|---|---|
| 0341904 | 5/1989 | European Pat. Off. . |
| 0387777 | 9/1990 | European Pat. Off. . |
| 9100916 | 1/1991 | WIPO . |
| 9111459 | 8/1991 | WIPO . |
| 9204918 | 4/1992 | WIPO . |

OTHER PUBLICATIONS

Seno et al. (1991), "Two cDNAs encoding novel human FGF receptor", *Biochem. Biophys. Acta* 1089:244–246.

Theillet et al. (1989), "Amplification of FGF-related genes in human tumors:possible involvement of HST in breast carcinomas", *Oncogene* 4:915–922.

Hou, et al., "Fibroblast growth factor receptors from liver vary in three structural domains," *Science* 251:665–668 (1991).

Isacchi, et al., "Complete sequence of a human receptor for acidic and basic fibroblast growth factors," *Nucleic Acids Research* 18(7):2616 (1990).

Keegan, et al., "Characterization of the FGFR–3 gene and its gene product," *Ann. N.Y. Acad. Sci.* 638:400–402 (1991).

Kiefer et al., "Molecular cloning of a human basic fibroblast growth factor receptor cDNA and expression of a biologically active extracellular domain in a baculovirus system," *Growth Factors*, 5:115–127 (1991).

McKeehan, W., "Growth factor receptors and prostate cell growth," *Cancer Surveys*, 11:165–175 (1991).

Nakamoto et al., "Basic fibroblast growth factor in human prostate cancer cells," *Cancer Research*, 52:571–577 (1992).

Olwin et al., "Cell type and tissue distribution of the fibroblast growth factor receptor," *J. Cell. Biochem.*, 39:443–154 (1989).

Partanen, et al., "FGFR–4, a novel acidic fibroblast growth factor receptor with a distinct expression pattern," *EMBO J.* 10(6):1347–1354 (1991).

Albino, A. et al., Induction of Growth Factor RNA Expression in Human Malignant Melanoma: Markers of Transformation. *Cancer Research.* 51:4815–4820 (1991).

Gaffey, M., The Search for a "Cancer Stain" in Diagnostic Surgical Pathology. *Amer. J. Clinical Path.* 96:679–680 (1991).

Halaban, R. et al., Paracrine Stimulation of Melanocytes by Keratinocytes Through Basic Fibroblast Growth Factor. *Annals of the New York Academy of Sciences*: 180–190 (1987).

Halaban, R. et al., bFGF as an Autocrine Growth Factor for Human Melanomas. *Oncogene Research.* 3:177–186 (1988).

Halaban, R. et al., bFGF is the Putative Natural Growth Factor for Human Melanocytes. *In Vitro Cellular & Developmental Biology.* 23:47–52 (1987).

Halaban, R. et al., Basic Fibroblast Growth Factor from Human Keratinocytes is a Natural Mitogen for Melanocytes. *J. Cell Biol.* 107:1611–1619 (1988).

Herlyn, M. et al., Growth–Regulatory Factors for Normal Premalignant, and Malignant Human Cells In vitro. *Advances in Cancer Research.* 54:213–234 (1990).

Rodeck, U., Basic Fibroblast Growth Factor in Human Melanoma. *Cancer Cells.* 3:308–311 (1991).

Rodeck, U. et al., Constitutive Expression of Multiple Growth Factor Genes by Melanoma Cells but Not Normal Melanocytes. *J. Investigative Dermatology.* 97:20–26 (1991).

Schulze–Osthoff, K. et al., In Situ Detection of Basic Fibroblast Growth Factor by Highly Specific Antibodies. *Amer. J. Pathology.* 137:85–92 (1990).

Scott, G. et al., Localization of Basic Fibroblast Growth Factor mRNA in Melanocytic Lesions by In Situ Hybridization. *J. Investigative Dermatology.* 96:318–322 (1991).

Weinberg, *Oncogenes and the Molecular Origins of Cancer*, Cold Spring Harbor Lab. Press, pp. 75–78 (1989).

Zouzias et al., *Clin. Res.* 38(2), 663A (1990).

Becker et al., *J. Cell. Biochem.* 16B (Suppl.), 300 (1992).

Nova et al., *J. Cut. Pathol.* 19(6), Dec. 1992.

Saito et al., *Biochem. Biophys. Res. Comm.* 174(1), 136–141 (1991).

Hattori et al., *Proc. Natl. Acad. Sci. USA* 87, 5983–5987 (1990).

Takahashi et al., *Biochem. Biophys. Res. Commun.* 177(1), 1–7 (1991).

Hattori et al., *Cancer Res.* 52, 3367–3371 (Jun. 1992).

Schweigerer et al., *Biochem. Biophys. Res. Comm.* 179(3), 1449–1454 (1991).

New et al., *J. Cell. Physiol.* 150, 320–326 (Feb. 1992).

*Primary Examiner*—Kenneth R. Horlick
*Attorney, Agent, or Firm*—Pennie & Edmonds LLP

[57] ABSTRACT

According to the present invention, processes for detecting the presence of neoplastic disease are provided. The processes involve the detection of a product associated with expression of genes that encode protein receptors for fibroblast growth factor in cells or a product present in a body fluid. Detection can be carried out in a variety of ways, such as by hybridization to detect the presence of mRNA or immunological assays to detect the presence of receptor protein.

24 Claims, No Drawings

PROCESS FOR THE DETECTION OF MALIGNANT MELANOMA

This application is a continuation of U.S. Ser. No. 07/900,646, filed Jun. 18, 1992, now abandoned.

This invention was made in part with Government support under Grant No. DK18811 from the National Institutes of Health. The Government may have certain rights in this invention.

FIELD OF THE INVENTION

This invention relates to processes for diagnosing cancer. In a more specific aspect it relates to a method for detecting melanoma.

BACKGROUND OF THE INVENTION

Despite improvements in surgical and radiological procedures and an increasingly large arsenal of drugs for treating cancer, cures for the many malignant neoplastic diseases remain elusive. The strides that have been made in reducing mortality have come largely from education programs which have heightened public awareness of the need for routine physical examination, coupled with improved techniques for detecting the presence of neoplastic disease at a sufficiently early stage to provide a favorable prognosis. Such improved techniques include immunoassays for an ever wider array of tumor associated antigens, such as carcinoembryonic antigen (CEA) and alphafetoprotein (AFP), and nucleic acid hybridization techniques. Nucleic acid hybridization can be used, for example, to diagnose the presence of chromosomal translocations associated with forms of cancer such as those identified with chronic myelogenous leukemia (CML), and the like.

Such advances are isolated and, accordingly, there remains a pressing need for better cancer diagnostics. In many cases, particularly those in which histological examination of biopsy material is used, it remains difficult to classify the kind of tumor which may be present. It is also difficult to differentiate malignancies from benign tumors and other non-malignant tissue abnormalities. Of perhaps even greater consequence to the patient, the techniques that are available are so lacking in sensitivity that early stage disease, the most opportune time for therapeutic intervention, is often missed entirely.

Malignant melanoma is an excellent example of a virulent cancer that is treatable by surgical removal with a high rate of success if detected before metastasis. After metastasis, however, the five year mortality rate is a shocking 97–99% using available chemotherapy and radiotherapy techniques (6,500 deaths in the United States in 1991). The shortcomings of modern treatments for melanoma take on heightened significance when it is appreciated that the incidence of this once relatively rare cancer is increasing annually at a rate of 4–10%, with 32,000 new cases in the United States in 1991.

Early detection of melanoma is complicated by the fact that many melanomas presented for diagnosis are either atypical in appearance (i.e., appear identical to non-melanocytic lesions), or are obscured by inflammation. Some melanomas are completely amelanotic (non-pigmented) and others are histologically similar to benign melanocytic growths. Thus, using classical histological techniques, it is frequently impossible to determine whether a lesion is actually a melanoma or whether it is a benign melanocytic growth or other type of carcinoma, for example, a sarcoma.

As the foregoing demonstrates, there clearly exists a pressing need for better techniques to detect and classify neoplastic diseases like melanoma. The present invention satisfies this need and provides related advantages as well.

SUMMARY OF THE INVENTION

According to the present invention, methods for detecting the presence of neoplastic disease are provided. The methods involve the detection of a product associated with expression of a gene which encodes a protein receptor for fibroblast growth factor (FGF) in cells or a body fluid, such as, for example, blood, serum or urine. When an assay is performed directly on suspect cells, the target product can be either the messenger RNA (mRNA) transcription product of the gene encoding the receptor or the receptor protein itself. In the case of body fluid and histopathologic analysis, the target expression product will be the receptor protein. Detection of the receptor can be accomplished by any technique which is specific for the protein. For example, immunological techniques employing antibodies to the receptor or a portion thereof that form a detectable antibody/receptor complex can be used. Techniques for detecting mRNA that employ nucleic acid hybridization are also useful for directly assaying suspect cells. These techniques use a nucleic acid probe having a nucleotide sequence that is complementary to that of the receptor. The probe is allowed to bind with the target RNA in a manner that permits detection of the resulting duplex using art established techniques.

DETAILED DESCRIPTION OF THE INVENTION

Fibroblast growth factor (FGF) is an almost ubiquitous protein that is highly multifunctional and present in many tissues. For this reason, it has generally been thought to act in vivo on the same cell types in which it acts in vitro. Surprisingly, however, it has been found that contrary to all of the predictions made from the results using cells in culture, the receptor for FGF is differentially expressed in vivo. For example, neoplastic tissues and cells after injury have elevated levels of receptor when compared to the low to absent levels in non-malignant (quiescent) tissue. Thus, these significantly higher levels of expression of the receptor gene by select neoplasms can be used to confirm the presence of such neoplasms. The higher levels of expression can be detected either by determining the presence of the receptor or its mRNA in cellular material, or by determining the presence of the receptor in body fluids as a result of sloughing from tumor cells.

The detection of a specific FGF receptor or its mRNA that is associated with malignant melanoma is particularly advantageous since they are both increased in amounts when compared to normal or benign lesions. Furthermore, the expression of FGF has been directly implicated in the transformation from normal melanocytes to melanoma (Halaban, R. et al., "bFGF As An Autocrine Growth Factor For Human Melanomas" *Oncogene Res.* 3:177–186 (1988) which is incorporated herein by reference). Accordingly, the improved assay of the invention will be described below with particular reference to its use for detecting malignant melanoma. However, the invention is not intended to be limited to malignant melanoma and can be applied to numerous other neoplasms including, but not limited to, subtyping of breast cancer, ovarian cancer, prostate hyperplasia, prostate carcinoma, astrocytoma, glioblastoma and similar diseases that are linked to FGF receptor expression.

As indicated above, the present invention provides means for determining the presence of select neoplastic disease. The process of the present invention comprises assaying a suitable sample for the presence of a product indicative of elevated levels of expression of the gene for FGF receptor protein and/or the receptor protein itself. The receptor (hereinafter referred to as "FGFR") is a cell surface protein receptor of which there are numerous subtypes and isoforms, each potentially specific for a particular cell type, more highly expressed in malignant than in non-malignant tissue. The target product of the gene expression to be assayed can either be FGFR itself or the mRNA encoding FGFR. These products can be detected by any suitable means for detection of specific amino acid or nucleic acid sequences. Preferred for this purpose are immunological techniques for detecting FGFR and nucleic acid hybridization techniques for detecting mRNA encoding FGFR.

Immunological and hybridization techniques for assaying proteins and mRNA are generally well known in the art and, accordingly, will not be described in detail. However, immunological techniques that can be used for detecting FGFR in a fluid sample such as blood, serum or urine, for example, include competitive immunoassays that employ an antibody specific for the receptor. Such assays can also typically employ a labeled receptor as a second reagent which competes for the captive antibody with receptor present in the sample. The labeled receptor is typically conjugated with a moiety which permits direct or indirect detection. Among the useful labels are radioactive nuclides such as $^{35}$S enzymatic moieties that cause a color change, or luminescence-generating reactions with suitable substrates. Such enzymes include, for example, luciferase, horseradish peroxidase and alkaline phosphatase. Fluorescent labels can also be used. Alternatively, the labeled receptor can be conjugated with a moiety which is recognized by another reagent which permits detection. For example, the receptor can be bound to biotin which will bind to a detectable avidin derivative, e.g., avidin conjugated with an enzyme as described above.

Another immunological process useful for detecting FGFR in fluid samples is the two-site or "sandwich" assay. This assay typically uses two antibody preparations, one of which is specific for FGFR and is bound, or capable of being bound, to a solid phase to separate FGFR from other material present in the sample. The second antibody preparation also binds FGFR and is labeled to permit detection of the antibody (solid phase):FGFR:antibody (labeled) complex after the appropriate contacting of the sample with the antibody reagents.

A third and presently preferred immunological technique, particularly for detection of melanoma, is the direct immunostaining of sections of biopsy material using anti-FGFR antibodies. Frozen sections or paraffin-fixed sections can be used. The anti-FGFR antibodies can be directly labeled with an enzyme such as peroxidase in order to generate a color reaction when substrate is added to the section. Preferably, however, the section is incubated with the anti-FGFR antibody, treated with a biotinylated antibody against the species of origin of the primary antibody, and then exposed to a complex of avidin and enzyme to increase the amount of enzyme present on the section and thereby increase the sensitivity of the process. A detailed description of this preferred process follows below. However, before doing so it should be noted that the antibodies useful in any of these immunological processes can be either polyclonal or monoclonal in nature and the species of origin, e.g., rabbit, goat, rat or murine, is not a critical feature of the invention. In addition, functional fragments of antibodies such as Fab, (Fab')$_2$ and peptides having an FGFR binding region can be employed. The means for obtaining such antibodies and fragments are also well known to those skilled in the art and will not be described in detail.

An antigen suitable for use in obtaining the antibodies useful in the practice of the present invention is, of course, of the FGF receptors, whose cloning and expression are described, for example, in Isacchi et al., "Complete Sequence of a Human Receptor for Acidic and Basic Fibroblast Growth Factors", *Nucleic Acid Res.* 18:1906 (1990) and in Kiefer et al., "Molecular Cloning of A Human Basic FGF Receptor cDNA and Expression of a Biologically Active Extracellular Domain in a Baculovirus System", *Growth Factors* 5:115–119 (1991), which are incorporated herein by reference. Fragments of FGFR may also be used as the antigen for production of either monoclonal or polyclonal antibodies to FGFR(s). One such antigen is the extracellular domain of FGFR. The preparation of polyclonal and monoclonal antibodies is described in Goding, J. W., *Monoclonal Antibodies: Principles and Practice*, Academic Press, London, NW1 (1986) and Groper, T. G., *The Tools of Biochemistry*, John Wiley & Sons, New York (1977), which are incorporated herein by reference.

The DNA sequence and encoded amino acids of a full length clone flg (FGFR-1), encoding a human receptor for acidic and basic fibroblast growth factors is set forth in SEQ ID NO. 1. The extracellular domain is included in amino acids 1–376 of SEQ ID NO. 1 and 1–374 of flg5 (Kiefer et al.), which lacks the Arg Met of SEQ ID NO. 1, residues 148–149.

A process for detecting the presence of FGFR in a paraffin-fixed section of biopsy material using a monoclonal or polyclonal antibody to FGFR, the preparation of which is described below, involves the following steps:

1. Incubate the section in 3% hydrogen peroxide for three (3) to five (5) minutes (depending on the antibody used) to quench endogenous peroxidase activity.

2. Wash section in phosphate-buffered saline (PBS) containing 0.1–0.5% Triton for 15–30 minutes depending on the antibody used as determined by optimization procedures.

3. Preincubate section for 20 minutes with a 1.5% solution in PBS-0.3% Triton (Sigma, St. Louis, Mo.) of a blocking serum comprising non-specific antibody of the same species as the anti-FGFR antibody (e.g., an antibody of murine origin), to saturate non-specific binding sites reactive with the anti-FGFR antibody.

4. Blot excess serum from the section.

5. Incubate section at 4° C. for 16–20 hours with "anti-FGFR antibody solution," prepared as described below.

6. After incubation with anti-FGFR, wash section for fifteen (15) minutes with PBS-0.3% Triton to remove non-specifically bound antibody.

7. Incubate sections with biotinylated anti-mouse antibody (commercially available from Vector Laboratories, Burlingame, Calif.) diluted in PBS-0.3% Triton containing 1.5% of the blocking serum of step 3 for 45 minutes at room temperature.

8. Wash section with PBS-0.3% Triton for fifteen (15) minutes.

9. Incubate section for 30 minutes to one (1) hour with avidin conjugated with peroxidase (ABC complex from Vector), diluted in PBS-0.3% Triton prepared thirty (30) minutes before use.

10. Wash section with PBS-0.3% Triton for fifteen (15) minutes.

11. Incubate section for twenty (20) minutes in peroxidase substrate solution (aminoethylcarbozate from Sigma) in DMSO and 50 mM acetate buffer (pH 5.0), containing 0.01% hydrogen peroxidase.

12. Wash section in deionized water for ten (10) minutes.

13. Counterstain section with hematoxylin (Fisher Chemicals, Tustin, Calif.) and mount slide with crystal mount.

14. Read section under a microscope comparing color versus lack of color presentation. Color development indicates a malignant lesion.

As can be seen in Table 1, malignant melanocytes stain positively using the techniques described above. However, benign melanocytes stain negatively using the above-described method, thus establishing selective expression of the detected protein in the neoplasia.

TABLE I

Antibody to Extracellular Domain of FGF Receptor FGFR

| LESION | CLINICAL[1] | STAINING[2] | COMMENT |
|---|---|---|---|
| melanoma | met, amelanotic | +++ | |
| melanoma | SST, CLIV | +++ | |
| melanoma | MMSST CLIV | +++ | |
| melanoma | SST, CLIV, B1.01 | +++ | |
| melanoma | SST | +++ | some epidermal staining |
| melanoma | SST, halonevus, inflammation | ++ | |
| melanoma | nodular type | ++ | |
| melanoma | SST | ++ | |
| melanoma | SST | +++ | some epidermal staining |
| melanoma | (LMM) | ++ | |
| melanoma | SST | ++ | |
| melanoma | large inflammatory halo nevus, minimal deviation melanoma | +++ | some epidermal staining |
| melanoma | SST, CLIV | ++ | |
| melanoma | NT | + | |
| melanoma | SST, CLIV | +++ | |
| melanoma | SST, CLIII | ++ | |
| melanoma | SST | ++ | no counterstain |
| melanoma | SST | ++ | some blood vessel (+) staining |
| melanoma | SST, CLII | ++ | no counterstain |
| melanoma | SST | + | |
| melanoma | NT, SST | ++ | |
| melanoma | SST | ++ | |
| melanoma | SST, NT | ++ | |
| melanoma | (MM) SST | ++ | |
| melanoma | SST | +++ | some epidermal staining |
| nevi | Bgn intradermal nevus | − | |
| nevi | Bgn intradermal nevus | − | |
| nevi | Bgn compound nevus | − | some blood vessel staining |
| nevi | Bgn compound nevus | − | |
| nevi | SLIN pigmented compound nevus | − | |
| nevi | Bgn pigmented intradermal nevus | − | |
| nevi | Bgn intradermal nevus | − | |
| nevi | SLIN pigmented compound nevus | − | some epidermal staining |
| nevi | Bgn neurotized nevus | − | |
| nevi | Bgn pigmented compound nevus | − | |
| nevi | SLIN pigmented compound nevus | − | |
| nevi | Bgn intradermal nevus | + | some nevus staining |
| nevi | Bgn intradermal nevus | − | |
| nevi | Bgn intradermal nevus | − | minimal epidermal staining |
| nevi | Bgn compound nevus | − | |

TABLE I-continued

Antibody to Extracellular Domain of FGF Receptor FGFR

| LESION | CLINICAL[1] | STAINING[2] | COMMENT |
|---|---|---|---|
| nevi | Bgn intradermal nevus | − | |
| nevi | Bgn compound nevus | − | |
| nevi | Bgn compound nevus | − | |
| nevi | blue nevus, heavy pigment | − | |
| nevi | bgn blue nevus, heavy pigment | − | |
| nevi | compound bgn Spitz nevus | − | |

[1]Clinical abbreviations:
SST = Superficial Spreading
MMSST = Malignant Melanoma Superficial Spreading
NT = Nodular Type
BGN = Benign
LMM = Lentigo Malignant Melanoma
CL = Clark's Level, e.g., depth of the melanoma from the epidermis
SLIN = Slightly Inflamed
B = Breslow Level, e.g., actual depth in millimeters from the epidermis
[2]Staining Level:
− = no staining
+ = minimal (light)
++ = intermediate
+++ = maximal (dark)

The lesions used in this study were obtained from human biopsy samples. The clinical terminology and staining determinations are described in W. F. Lever, *Histopathology of the Skin*, 7th ed., J. B. Lippincott Company, Philadelphia (1990).

As pointed out above, mRNA transcribed from the receptor gene is an alternative target to the receptor itself when an assay is performed directly on suspected cancer cells. In such assays, a nucleic acid probe having a nucleotide sequence complementary to the target mRNA is added to the cells in a manner which permits the probe to hybridize to the mRNA encoding the receptor. The length of the probe can, of course, be any length adequate to permit a diagnostic result when high stringency hybridization conditions are used. As used herein, "high stringency conditions" means conditions of low salt concentration and elevated temperature whereby the cRNA probe for FGFR will anneal to the RNA encoding FGFR alone and not non-specifically to other mRNA. Accordingly, the length of the probe is preferably at least about 20 nucleotides, and more preferably at least about 50 nucleotides, and will not normally exceed about 500 nucleotides.

The probe can be labeled to permit its direct detection. While a variety of labels are useful, since the sample to be assayed will typically be a paraffin-embedded section from a tissue biopsy, it is preferred that the label be one which can generate a color reaction when a suitable substrate is added to the section after any unbound probe has been removed by washing. Among suitable labels, therefore, are enzymes which, in the presence of a suitable substrate, generate a color. These include various peroxidases, such as horseradish peroxidase, alkaline phosphatase and the like in a particular embodiment the probe is labeled with digoxin.

Although direct labeling can be used, it is preferred to label the probe with biotin and to treat the hybridized probe with an avidin/enzyme complex as described above for the immunostaining process. This procedure can conveniently be done by synthesizing the probe using a nucleotide which is biotinylated. Biotinylated uracil triphosphate is preferred for this purpose.

A preferred process for detecting mRNA encoding FGFR in a standard paraffin-fixed section of biopsy material using, for example, a biotinylated probe of a sequence derived for example from a sequence set forth in Kiefer et al., Isacchi et al., Keegan et al., "Characterization of the FGFR-3 Gene and its Gene Product", Ann. N.Y. Acad. Sci. 638:400-402 (1991), Hou et al. "Fibroblast Growth Factor Receptors From Liver Vary in Three Structural Domains", Science 251:665-668 (1991) or Partanen et al., "FGFR-4, A Novel Acidic Fibroblast Growth Factor Receptor With Distinct Expression Pattern", EMBO J. 10:1345-1354 (1991) or other related sequences corresponding to other parts of the many isoforms and subtypes of the FGF receptor, involves the following steps:

1. Prior to hybridization, wash the slide with the following reagents:

a. xylene (10 min.)

b. 100% ethanol (10 min.)

c. air dry (10 min.)

d. 95% ethanol (2 min.)

e. 80% ethanol (2 min.)

f. 70% ethanol (2 min.)

g. 2× SSPE buffer, 2× (5 min.)

h. Proteinase K (10 µ/ml), 37° C., (30 min.)

i. 0.1M TEA, 0.25% Acetic Anhydride; (10 min.)

j. 2× SSPE buffer, 2× (5 min.)

k. 0.1M Tris/glycine pH 7.0 (30 min.)

l. 2× SSPE buffer, 2× (3 min.)

m. 70% ethanol (3 min.)

n. 95% ethanol (3 min.)

o. air dry (2 hrs.).

2. Dilute probe to 800 ng/ml with buffer (recipe steps 2a–2f below) and apply to slide. Seal the coverslips and incubate overnight at 55° C. on a warm plate.

a. 5 ml deionized formamide b. 2 ml dextran sulfate c. 2 ml SSPE (20×)

d. 0.2 ml Denhardt's solution (50×)

e. 0.5 ml total RNA (from salmon sperm) (10 µg/ml)

f. 0.25 ml yeast tRNA (10 µg/ml).

3. Rinse with 4× SSPE for 20 minutes to remove coverslip followed by 3×10-minute rinses.

4. Rinse with 50% formamide/2× SSPE, 2× for 15 minutes at 48°–50° C.

5. Rinse with 2× SSPE buffer, 2× (10 min.)

6. Incubate with RNase, 37° C. (30 min.)

7. Rinse with 2× SSPE buffer, 2× (10 min.)

8. Rinse with 50% formamide/2× SSPE at 48°–50° C. (15 min.)

9. Rinse with 2× SSPE buffer (5 min.)

10. Rinse with 0.1M Tris Saline (5 min.)

11. Incubate section with avidin complex with alkaline phosphatase (Vector) for 1 hour at room temperature.

12. Rinse section with 0.1M Tris saline for 5 minutes (3×).

13. Incubate section with Fast Red solution for 8 hours (optionally with Levamisole, an inhibitor of endogenous alkaline phosphatase).

14. Rinse with deionized water 3×.

15. Counterstain with hematoxylin (optional).

16. Rinse with deionized water.

17. Mount section with crystal mount.

18. Read section under a microscope and look for color change.

As shown in Table 2, malignant melanocytes stain positively using the techniques described above. Benign melanocytes stain negatively using the same techniques, thus establishing that there is selective expression of the detected mRNAs in neoplastic cells. The lesions used in this study were obtained from human biopsy samples.

TABLE II

IN SITU HYBRIDIZATION OF FGFR mRNA PROBE (BIOTINYLATED)

| LESION | CLINICAL[1] | STAINING[2] | COMMENT |
|---|---|---|---|
| melanoma | SST | ++ | |
| melanoma | SST | ++ | grainy |
| melanoma | SST | ++ | |
| nevi (intradermal) | | – | |
| nevi (compound) | | – | |
| nevi (intradermal) | | – | some epidermal staining |

[1]Clinical abbreviations:
SST = Superficial Spreading
[2]Staining Level:
– = no staining
+ = minimal (light)
++ = intermediate
+++ = maximal (dark)

Although the invention has been described with reference to the presently-preferred embodiments, it should be understood that various modifications can be made without departing from the spirit of the invention. Accordingly, the invention is limited only by the following claims.

---

We claim:

1. A process for detecting malignant melanoma in a subject, comprising detecting, in a sample that contains melanocytes obtained from the subject, a first product indicative of elevated expression of a fibroblast growth factor receptor gene or a second product indicative of elevated amounts of a fibroblast growth factor receptor (FGFR), wherein detection of said first or second product in elevated expression or amount, respectively, compared to a control sample containing normal or benign melanocytes indicates the presence of malignant melanoma in said subject.

2. A process for detecting malignant melanoma in a subject, comprising detecting, in a sample that contains melanocytes obtained from the subject, a first product indicative of elevated expression of a fibroblast growth factor receptor gene or a second product indicative of elevated amounts of a fibroblast growth factor receptor (FGFR), wherein detection of said first or second product in elevated expression or amount, respectively, compared to a control sample containing normal or benign melanocytes indicates the presence of malignant melanoma in said subject; and detection is effected by contacting the sample obtained from the subject with an agent that binds to the extracellular domain of an FGFR or with a nucleic acid probe that includes a sequence of at least about 20 nucleotides that hybridizes under conditions of high stringency to nucleic acid encoding the extracellular domain of an FGFR.

3. The process of claim 2, wherein the detection of said product is accomplished by:
   (a) contacting the sample obtained from said subject with the agent; and
   (b) detecting the binding of said agent to said product, wherein the detection of the binding of said agent indicates the presence of malignant melanoma.

4. The agent of claim 3, wherein said process is an antibody or a functional fragment thereof.

5. The agent of claim 3, wherein said process is a nucleic acid probe.

6. The agent of claim 3, wherein said process is labelled with a detectable marker.

7. A process according to claim 3, wherein the product is a receptor protein.

8. A process according to claim 2, wherein an immunological process is used to detect the receptor protein.

9. The process of claim 8, wherein the sample is biopsied tissue and the immunological process comprises fixing the sample in paraffin; and treating the paraffin-fixed section of biopsy material with an antibody having specific reactivity with the receptor protein, removing unbound antibody from the section and detecting the antibody bound to receptor protein present in the section, wherein the detection of antibody bound to said receptor protein indicates the presence of malignant melanoma in said subject.

10. A process according to claim 9, wherein the bound antibody is detected by:
    (a) incubating the section with a second antibody capable of binding to the first antibody, wherein said second antibody is biotinylated;
    (b) removing unbound second antibody from the section;
    (c) incubating the section with complex of avidin and peroxidase;
    (d) removing unbound avidin/peroxidase complex from the section;
    (e) treating the section with a color forming substrate for peroxidase;
    (f) removing unbound substrate from the section; and
    (g) determining the amount of color formed to determine the presence of malignant malanoma.

11. A process according to claim 3, wherein the product is mRNA encoding the receptor protein.

12. A process according to claim 11, wherein the mRNA is detected by hybridization with a detectable nucleic acid probe having a nucleotide sequence sufficiently complementary to at least a portion of the mRNA to hybridize to said mRNA.

13. A process according to claim 12, wherein the probe is biotinylated.

14. A process according to claim 12, wherein the probe is labeled with digoxin.

15. A process according to claim 13 or 14, wherein hybridization of the probe to mRNA in said sample is detected by:
    (a) removal of unbound probe from the sample;
    (b) incubation of the sample with a complex of avidin and alkaline phosphatase;
    (c) removal of unbound avidin/alkaline phosphatase complex from the sample;
    (d) treatment of the sample with a color forming substrate for alkaline phosphatase;
    (e) removal of unbound substrate; and
    (f) determining the amount of color formed to determine the presence of malignant melanoma.

16. The process of claim 2, wherein the product is mRNA.

17. The process of claim 2, wherein the FGFR is FGFR-1.

18. The process of claim 12, wherein the FGFR is FGFR-1.

19. The process of claim 7, wherein the receptor is FGFR-1.

20. The process of claim 11, wherein the sample is biopsied tissue.

21. A process for detecting malignant melanoma in a subject, comprising detecting, in a sample that contains melanocytes obtained from the subject, a first product indicative of elevated expression of a fibroblast growth factor receptor gene or a second product indicative of elevated amounts of a fibroblast growth factor receptor (FGFR), wherein detection of said first or second product in elevated expression or amount, respectively, compared to a control sample containing normal or benign melanocytes indicates the presence of malignant melanoma in said subject; and detection is effected by contacting the sample obtained from said subject with an agent that binds to FGFR-1 or with a nucleic acid probe that includes a sequence of at least about 20 nucleotides that hybridizes under conditions of high stringency to nucleic acid encoding FGFR-1.

22. The process of claim 21, wherein the detection of the product is accomplished by:
    (a) contacting the sample obtained from the subject with the agent; and
    (b) detecting the binding of the agent to the product, wherein the detection of the binding of the agent indicates the presence of malignant melanoma.

23. The process of claim 21, wherein the agent is an antibody or a functional fragment thereof.

24. The process of claim 21, wherein the agent is a nucleic acid probe.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2469 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:

-continued (A) NAME/KEY: Coding Sequence
(B) LOCATION: 1...2466
(D) OTHER INFORMATION:

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | TGG | AGC | TGG | AAG | TGC | CTC | CTC | TTC | TGG | GCT | GTG | CTG | GTC | ACA | GCC | 48 |
| Met | Trp | Ser | Trp | Lys | Cys | Leu | Leu | Phe | Trp | Ala | Val | Leu | Val | Thr | Ala | |
| 1 | | | | 5 | | | | | 10 | | | | | 15 | | |
| ACA | CTC | TGC | ACC | GCT | AGG | CCG | TCC | CCG | ACC | TTG | CCT | GAA | CAA | GCC | CAG | 96 |
| Thr | Leu | Cys | Thr | Ala | Arg | Pro | Ser | Pro | Thr | Leu | Pro | Glu | Gln | Ala | Gln | |
| | | | 20 | | | | | 25 | | | | | 30 | | | |
| CCC | TGG | GGA | GCC | CCT | GTG | GAA | GTG | GAG | TCC | TTC | CTG | GTC | CAC | CCC | GGT | 144 |
| Pro | Trp | Gly | Ala | Pro | Val | Glu | Val | Glu | Ser | Phe | Leu | Val | His | Pro | Gly | |
| | | 35 | | | | | 40 | | | | | 45 | | | | |
| GAC | CTG | CTG | CAG | CTT | CGC | TGT | CGG | CTG | CGG | GAC | GAT | GTG | CAG | AGC | ATC | 192 |
| Asp | Leu | Leu | Gln | Leu | Arg | Cys | Arg | Leu | Arg | Asp | Asp | Val | Gln | Ser | Ile | |
| | 50 | | | | | 55 | | | | | 60 | | | | | |
| AAC | TGG | CTG | CGG | GAC | GGG | GTG | CAG | CTG | GCG | GAA | AGC | AAC | CGC | ACC | CGC | 240 |
| Asn | Trp | Leu | Arg | Asp | Gly | Val | Gln | Leu | Ala | Glu | Ser | Asn | Arg | Thr | Arg | |
| 65 | | | | | 70 | | | | | 75 | | | | | 80 | |
| ATC | ACA | GGG | GAG | GAG | GTG | GAG | GTG | CAG | GAC | TCC | GTG | CCC | GCA | GAC | TCC | 288 |
| Ile | Thr | Gly | Glu | Glu | Val | Glu | Val | Gln | Asp | Ser | Val | Pro | Ala | Asp | Ser | |
| | | | | 85 | | | | | 90 | | | | | 95 | | |
| GGC | CTC | TAT | GCT | TGC | GTA | ACC | AGC | AGC | CCC | TCG | GGC | AGT | GAC | ACC | ACC | 336 |
| Gly | Leu | Tyr | Ala | Cys | Val | Thr | Ser | Ser | Pro | Ser | Gly | Ser | Asp | Thr | Thr | |
| | | | 100 | | | | | 105 | | | | | 110 | | | |
| TAC | TTC | TCC | GTC | AAT | GTT | TCA | GAT | GCT | CTC | CCC | TCC | TCG | GAG | GAT | GAT | 384 |
| Tyr | Phe | Ser | Val | Asn | Val | Ser | Asp | Ala | Leu | Pro | Ser | Ser | Glu | Asp | Asp | |
| | | 115 | | | | | 120 | | | | | 125 | | | | |
| GAT | GAT | GAT | GAT | GAC | TCC | TCT | TCA | GAG | GAG | AAA | GAA | ACA | GAT | AAC | ACC | 432 |
| Asp | Asp | Asp | Asp | Asp | Ser | Ser | Ser | Glu | Glu | Lys | Glu | Thr | Asp | Asn | Thr | |
| | 130 | | | | | 135 | | | | | 140 | | | | | |
| AAA | CCA | AAC | CGT | ATG | CCC | GTA | GCT | CCA | TAT | TGG | ACA | TCC | CCA | GAA | AAG | 480 |
| Lys | Pro | Asn | Arg | Met | Pro | Val | Ala | Pro | Tyr | Trp | Thr | Ser | Pro | Glu | Lys | |
| 145 | | | | | 150 | | | | | 155 | | | | | 160 | |
| ATG | GAA | AAG | AAA | TTG | CAT | GCA | GTG | CCG | GCT | GCC | AAG | ACA | GTG | AAG | TTC | 528 |
| Met | Glu | Lys | Lys | Leu | His | Ala | Val | Pro | Ala | Ala | Lys | Thr | Val | Lys | Phe | |
| | | | | 165 | | | | | 170 | | | | | 175 | | |
| AAA | TGC | CCT | TCC | AGT | GGG | ACC | CCA | AAC | CCC | ACA | CTG | CGC | TGG | TTG | AAA | 576 |
| Lys | Cys | Pro | Ser | Ser | Gly | Thr | Pro | Asn | Pro | Thr | Leu | Arg | Trp | Leu | Lys | |
| | | | 180 | | | | | 185 | | | | | 190 | | | |
| AAT | GGC | AAA | GAA | TTC | AAA | CCT | GAC | CAC | AGA | ATT | GGA | GGC | TAC | AAG | GTC | 624 |
| Asn | Gly | Lys | Glu | Phe | Lys | Pro | Asp | His | Arg | Ile | Gly | Gly | Tyr | Lys | Val | |
| | | 195 | | | | | 200 | | | | | 205 | | | | |
| CGT | TAT | GCC | ACC | TGG | AGC | ATC | ATA | ATG | GAC | TCT | GTG | GTG | CCC | TCT | GAC | 672 |
| Arg | Tyr | Ala | Thr | Trp | Ser | Ile | Ile | Met | Asp | Ser | Val | Val | Pro | Ser | Asp | |
| | 210 | | | | | 215 | | | | | 220 | | | | | |
| AAG | GGC | AAC | TAC | ACC | TGC | ATT | GTG | GAG | AAT | GAG | TAC | GGC | AGC | ATC | AAC | 720 |
| Lys | Gly | Asn | Tyr | Thr | Cys | Ile | Val | Glu | Asn | Glu | Tyr | Gly | Ser | Ile | Asn | |
| 225 | | | | | 230 | | | | | 235 | | | | | 240 | |
| CAC | ACA | TAC | CAG | CTG | GAT | GTC | GTG | GAG | CGG | TCC | CCT | CAC | CGG | CCC | ATC | 768 |
| His | Thr | Tyr | Gln | Leu | Asp | Val | Val | Glu | Arg | Ser | Pro | His | Arg | Pro | Ile | |
| | | | | 245 | | | | | 250 | | | | | 255 | | |
| CTG | CAA | GCA | GGG | TTG | CCC | GCC | AAC | AAA | ACA | GTG | GCC | CTG | GGT | AGC | AAC | 816 |
| Leu | Gln | Ala | Gly | Leu | Pro | Ala | Asn | Lys | Thr | Val | Ala | Leu | Gly | Ser | Asn | |
| | | | 260 | | | | | 265 | | | | | 270 | | | |
| GTG | GAG | TTC | ATG | TGT | AAG | GTG | TAC | AGT | GAC | CCG | CAG | CCG | CAC | ATC | CAG | 864 |
| Val | Glu | Phe | Met | Cys | Lys | Val | Tyr | Ser | Asp | Pro | Gln | Pro | His | Ile | Gln | |
| | | 275 | | | | | 280 | | | | | 285 | | | | |
| TGG | CTA | AAG | CAC | ATC | GAG | GTG | AAT | GGG | AGC | AAG | ATT | GGC | CCA | GAC | AAC | 912 |
| Trp | Leu | Lys | His | Ile | Glu | Val | Asn | Gly | Ser | Lys | Ile | Gly | Pro | Asp | Asn | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 290 |     |     |     |     | 295 |     |     |     |     | 300 |     |     |     |      |
| CTG | CCT | TAT | GTC | CAG | ATC | TTG | AAG | ACT | GCT | GGA | GTT | AAT | ACC | ACC | GAC | 960  |
| Leu | Pro | Tyr | Val | Gln | Ile | Leu | Lys | Thr | Ala | Gly | Val | Asn | Thr | Thr | Asp |      |
| 305 |     |     |     | 310 |     |     |     |     | 315 |     |     |     |     | 320 |     |      |
| AAA | GAG | ATG | GAG | GTG | CTT | CAC | TTA | AGA | AAT | GTC | TCC | TTT | GAG | GAC | GCA | 1008 |
| Lys | Glu | Met | Glu | Val | Leu | His | Leu | Arg | Asn | Val | Ser | Phe | Glu | Asp | Ala |      |
|     |     |     |     | 325 |     |     |     |     | 330 |     |     |     |     | 335 |     |      |
| GGG | GAG | TAT | ACG | TGC | TTG | GCG | GGT | AAC | TCT | ATC | GGA | CTC | TCC | CAT | CAC | 1056 |
| Gly | Glu | Tyr | Thr | Cys | Leu | Ala | Gly | Asn | Ser | Ile | Gly | Leu | Ser | His | His |      |
|     |     |     | 340 |     |     |     |     | 345 |     |     |     |     | 350 |     |     |      |
| TCT | GCA | TGG | TTG | ACC | GTT | CTG | GAA | GCC | CTG | GAA | GAG | AGG | CCG | GCA | GTG | 1104 |
| Ser | Ala | Trp | Leu | Thr | Val | Leu | Glu | Ala | Leu | Glu | Glu | Arg | Pro | Ala | Val |      |
|     |     | 355 |     |     |     |     | 360 |     |     |     |     | 365 |     |     |     |      |
| ATG | ACC | TCG | CCC | CTG | TAC | CTG | GAG | ATC | ATC | ATC | TAT | TGC | ACA | GGG | GCC | 1152 |
| Met | Thr | Ser | Pro | Leu | Tyr | Leu | Glu | Ile | Ile | Ile | Tyr | Cys | Thr | Gly | Ala |      |
|     | 370 |     |     |     |     | 375 |     |     |     |     | 380 |     |     |     |     |      |
| TTC | CTC | ATC | TCC | TGC | ATG | GTG | GGG | TCG | GTC | ATC | GTC | TAC | AAG | ATG | AAG | 1200 |
| Phe | Leu | Ile | Ser | Cys | Met | Val | Gly | Ser | Val | Ile | Val | Tyr | Lys | Met | Lys |      |
| 385 |     |     |     |     | 390 |     |     |     |     | 395 |     |     |     |     | 400 |      |
| AGT | GGT | ACC | AAG | AAG | AGT | GAC | TTC | CAC | AGC | CAG | ATG | GCT | GTG | CAC | AAG | 1248 |
| Ser | Gly | Thr | Lys | Lys | Ser | Asp | Phe | His | Ser | Gln | Met | Ala | Val | His | Lys |      |
|     |     |     |     | 405 |     |     |     |     | 410 |     |     |     |     | 415 |     |      |
| CTG | GCC | AAG | AGC | ATC | CCT | CTG | CGC | AGA | CAG | GTA | ACA | GTG | TCT | GCT | GAC | 1296 |
| Leu | Ala | Lys | Ser | Ile | Pro | Leu | Arg | Arg | Gln | Val | Thr | Val | Ser | Ala | Asp |      |
|     |     |     | 420 |     |     |     |     | 425 |     |     |     |     | 430 |     |     |      |
| TCC | AGT | GCA | TCC | ATG | AAC | TCT | GGG | GTT | CTT | CTG | GTT | CGG | CCA | TCA | CGG | 1344 |
| Ser | Ser | Ala | Ser | Met | Asn | Ser | Gly | Val | Leu | Leu | Val | Arg | Pro | Ser | Arg |      |
|     |     | 435 |     |     |     |     | 440 |     |     |     |     | 445 |     |     |     |      |
| CTC | TCC | TCC | AGT | GGG | ACT | CCC | ATG | CTA | GCA | GGG | GTC | TCT | GAG | TAT | GAG | 1392 |
| Leu | Ser | Ser | Ser | Gly | Thr | Pro | Met | Leu | Ala | Gly | Val | Ser | Glu | Tyr | Glu |      |
|     | 450 |     |     |     |     | 455 |     |     |     |     | 460 |     |     |     |     |      |
| CTT | CCC | GAA | GAC | CCT | CGC | TGG | GAG | CTG | CCT | CGG | GAC | AGA | CTG | GTC | TTA | 1440 |
| Leu | Pro | Glu | Asp | Pro | Arg | Trp | Glu | Leu | Pro | Arg | Asp | Arg | Leu | Val | Leu |      |
| 465 |     |     |     |     | 470 |     |     |     |     | 475 |     |     |     |     | 480 |      |
| GGC | AAA | CCC | CTG | GGA | GAG | GGC | TGC | TTT | GGG | CAG | GTG | GTG | TTG | GCA | GAG | 1488 |
| Gly | Lys | Pro | Leu | Gly | Glu | Gly | Cys | Phe | Gly | Gln | Val | Val | Leu | Ala | Glu |      |
|     |     |     |     | 485 |     |     |     |     | 490 |     |     |     |     | 495 |     |      |
| GCT | ATC | GGG | CTG | GAC | AAG | GAC | AAA | CCC | AAC | CGT | GTG | ACC | AAA | GTG | GCT | 1536 |
| Ala | Ile | Gly | Leu | Asp | Lys | Asp | Lys | Pro | Asn | Arg | Val | Thr | Lys | Val | Ala |      |
|     |     |     | 500 |     |     |     |     | 505 |     |     |     |     | 510 |     |     |      |
| GTG | AAG | ATG | TTG | AAG | TCG | GAC | GCA | ACA | GAG | AAA | GAC | TTG | TCA | GAC | CTG | 1584 |
| Val | Lys | Met | Leu | Lys | Ser | Asp | Ala | Thr | Glu | Lys | Asp | Leu | Ser | Asp | Leu |      |
|     |     | 515 |     |     |     |     | 520 |     |     |     |     | 525 |     |     |     |      |
| ATC | TCA | GAA | ATG | GAG | ATG | ATG | AAG | ATG | ATC | GGG | AAG | CAT | AAG | AAT | ATC | 1632 |
| Ile | Ser | Glu | Met | Glu | Met | Met | Lys | Met | Ile | Gly | Lys | His | Lys | Asn | Ile |      |
|     | 530 |     |     |     |     | 535 |     |     |     |     | 540 |     |     |     |     |      |
| ATC | AAC | CTG | CTG | GGG | GCC | TGC | ACG | CAG | GAT | GGT | CCC | TTG | TAT | GTC | ATC | 1680 |
| Ile | Asn | Leu | Leu | Gly | Ala | Cys | Thr | Gln | Asp | Gly | Pro | Leu | Tyr | Val | Ile |      |
| 545 |     |     |     |     | 550 |     |     |     |     | 555 |     |     |     |     | 560 |      |
| GTG | GAG | TAT | GCC | TCC | AAG | GGC | AAC | CTG | CGG | GAG | TAC | CTG | CAG | GCC | CGG | 1728 |
| Val | Glu | Tyr | Ala | Ser | Lys | Gly | Asn | Leu | Arg | Glu | Tyr | Leu | Gln | Ala | Arg |      |
|     |     |     |     | 565 |     |     |     |     | 570 |     |     |     |     | 575 |     |      |
| AGG | CCC | CCA | GGG | CTG | GAA | TAC | TGC | TAC | AAC | CCC | AGC | CAC | AAC | CCA | GAG | 1776 |
| Arg | Pro | Pro | Gly | Leu | Glu | Tyr | Cys | Tyr | Asn | Pro | Ser | His | Asn | Pro | Glu |      |
|     |     |     | 580 |     |     |     |     | 585 |     |     |     |     | 590 |     |     |      |
| GAG | CAG | CTC | TCC | TCC | AAG | GAC | CTG | GTG | TCC | TGC | GCC | TAC | CAG | GTG | GCC | 1824 |
| Glu | Gln | Leu | Ser | Ser | Lys | Asp | Leu | Val | Ser | Cys | Ala | Tyr | Gln | Val | Ala |      |
|     |     | 595 |     |     |     |     | 600 |     |     |     |     | 605 |     |     |     |      |
| GGA | GGC | ATG | GAG | TAT | CTG | GCC | TCC | AAG | AAG | TGC | ATA | CAC | CGA | GAC | CTG | 1872 |
| Gly | Gly | Met | Glu | Tyr | Leu | Ala | Ser | Lys | Lys | Cys | Ile | His | Arg | Asp | Leu |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 610 |     |     |     |     | 615 |     |     |     |     | 620 |     |     |      |
| GCA | GCC | AGG | AAT | GTC | CTG | GTG | ACA | GAG | GAC | AAT | GTG | ATG | AAG | ATA | GCA | 1920 |
| Ala | Ala | Arg | Asn | Val | Leu | Val | Thr | Glu | Asp | Asn | Val | Met | Lys | Ile | Ala |      |
| 625 |     |     |     |     | 630 |     |     |     |     | 635 |     |     |     |     | 640 |      |
| GAC | TTT | GGC | CTC | GCA | CGG | GAC | ATT | CAC | CAC | ATC | GAC | TAC | TAT | AAA | AAG | 1968 |
| Asp | Phe | Gly | Leu | Ala | Arg | Asp | Ile | His | His | Ile | Asp | Tyr | Tyr | Lys | Lys |      |
|     |     |     |     | 645 |     |     |     |     | 650 |     |     |     |     | 655 |     |      |
| ACA | ACC | AAC | GGC | CGA | CTG | CCT | GTG | AAG | TGG | ATG | GCA | CCC | GAG | GCA | TTA | 2016 |
| Thr | Thr | Asn | Gly | Arg | Leu | Pro | Val | Lys | Trp | Met | Ala | Pro | Glu | Ala | Leu |      |
|     |     |     | 660 |     |     |     |     | 665 |     |     |     |     | 670 |     |     |      |
| TTT | GAC | CGG | ATC | TAC | ACC | CAC | CAG | AGT | GAT | GTG | TGG | TCT | TTC | GGG | GTG | 2064 |
| Phe | Asp | Arg | Ile | Tyr | Thr | His | Gln | Ser | Asp | Val | Trp | Ser | Phe | Gly | Val |      |
|     |     | 675 |     |     |     |     | 680 |     |     |     |     | 685 |     |     |     |      |
| CTC | CTG | TGG | GAG | ATC | TTC | ACT | CTG | GGC | GGC | TCC | CCA | TAC | CCC | GGT | GTG | 2112 |
| Leu | Leu | Trp | Glu | Ile | Phe | Thr | Leu | Gly | Gly | Ser | Pro | Tyr | Pro | Gly | Val |      |
|     | 690 |     |     |     |     | 695 |     |     |     |     | 700 |     |     |     |     |      |
| CCT | GTG | GAG | GAA | CTT | TTC | AAG | CTG | CTG | AAG | GAG | GGT | CAC | CGC | ATG | GAC | 2160 |
| Pro | Val | Glu | Glu | Leu | Phe | Lys | Leu | Leu | Lys | Glu | Gly | His | Arg | Met | Asp |      |
| 705 |     |     |     |     | 710 |     |     |     |     | 715 |     |     |     |     | 720 |      |
| AAG | CCC | AGT | AAC | TGC | ACC | AAC | GAG | CTG | TAC | ATG | ATG | ATG | CGG | GAC | TGC | 2208 |
| Lys | Pro | Ser | Asn | Cys | Thr | Asn | Glu | Leu | Tyr | Met | Met | Met | Arg | Asp | Cys |      |
|     |     |     |     | 725 |     |     |     |     | 730 |     |     |     |     | 735 |     |      |
| TGG | CAT | GCA | GTG | CCC | TCA | CAG | AGA | CCC | ACC | TTC | AAG | CAG | CTG | GTG | GAA | 2256 |
| Trp | His | Ala | Val | Pro | Ser | Gln | Arg | Pro | Thr | Phe | Lys | Gln | Leu | Val | Glu |      |
|     |     |     | 740 |     |     |     |     | 745 |     |     |     |     | 750 |     |     |      |
| GAC | CTG | GAC | CGC | ATC | GTG | GCC | TTG | ACC | TCC | AAC | CAG | GAG | TAC | CTG | GAC | 2304 |
| Asp | Leu | Asp | Arg | Ile | Val | Ala | Leu | Thr | Ser | Asn | Gln | Glu | Tyr | Leu | Asp |      |
|     |     | 755 |     |     |     |     | 760 |     |     |     |     | 765 |     |     |     |      |
| CTG | TCC | ATG | CCC | CTG | GAC | CAG | TAC | TCC | CCC | AGC | TTT | CCC | GAC | ACC | CGG | 2352 |
| Leu | Ser | Met | Pro | Leu | Asp | Gln | Tyr | Ser | Pro | Ser | Phe | Pro | Asp | Thr | Arg |      |
|     | 770 |     |     |     |     | 775 |     |     |     |     | 780 |     |     |     |     |      |
| AGC | TCT | ACG | TGC | TCC | TCA | GGG | GAG | GAT | TCC | GTC | TTC | TCT | CAT | GAG | CCG | 2400 |
| Ser | Ser | Thr | Cys | Ser | Ser | Gly | Glu | Asp | Ser | Val | Phe | Ser | His | Glu | Pro |      |
| 785 |     |     |     |     | 790 |     |     |     |     | 795 |     |     |     |     | 800 |      |
| CTG | CCC | GAG | GAG | CCC | TGC | CTG | CCC | CGA | CAC | CCA | GCC | CAG | CTT | GCC | AAT | 2448 |
| Leu | Pro | Glu | Glu | Pro | Cys | Leu | Pro | Arg | His | Pro | Ala | Gln | Leu | Ala | Asn |      |
|     |     |     |     | 805 |     |     |     |     | 810 |     |     |     |     | 815 |     |      |
| CGG | GGA | CTC | AAA | CGC | CGC | TGA |     |     |     |     |     |     |     |     |     | 2469 |
| Arg | Gly | Leu | Lys | Arg | Arg |     |     |     |     |     |     |     |     |     |     |      |
|     |     |     | 820 |     |     |     |     |     |     |     |     |     |     |     |     |      |

( 2 ) INFORMATION FOR SEQ ID NO:2:

( i ) SEQUENCE CHARACTERISTICS:
        ( A ) LENGTH: 822 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

| Met | Trp | Ser | Trp | Lys | Cys | Leu | Leu | Phe | Trp | Ala | Val | Leu | Val | Thr | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Leu | Cys | Thr | Ala | Arg | Pro | Ser | Pro | Thr | Leu | Pro | Glu | Gln | Ala | Gln |
|     |     |     | 20  |     |     |     |     | 25  |     |     |     |     | 30  |     |     |
| Pro | Trp | Gly | Ala | Pro | Val | Glu | Val | Glu | Ser | Phe | Leu | Val | His | Pro | Gly |
|     |     |     | 35  |     |     |     |     | 40  |     |     |     |     | 45  |     |     |
| Asp | Leu | Leu | Gln | Leu | Arg | Cys | Arg | Leu | Arg | Asp | Asp | Val | Gln | Ser | Ile |
|     |     | 50  |     |     |     |     | 55  |     |     |     |     | 60  |     |     |     |
| Asn | Trp | Leu | Arg | Asp | Gly | Val | Gln | Leu | Ala | Glu | Ser | Asn | Arg | Thr | Arg |

-continued

| | | | | | | | | | | | | | | | |
|---|---|---|---|---|---|---|---|---|---|---|---|---|---|---|---|
| 65 | | | | 70 | | | | 75 | | | | 80 | | | |
| Ile | Thr | Gly | Glu | Glu 85 | Val | Glu | Val | Gln 90 | Asp | Ser | Val | Pro | Ala | Asp 95 | Ser |
| Gly | Leu | Tyr | Ala 100 | Cys | Val | Thr | Ser | Ser 105 | Pro | Ser | Gly | Ser | Asp 110 | Thr | Thr |
| Tyr | Phe | Ser 115 | Val | Asn | Val | Ser | Asp 120 | Ala | Leu | Pro | Ser | Ser 125 | Glu | Asp | Asp |
| Asp 130 | Asp | Asp | Asp | Asp | Ser | Ser 135 | Ser | Glu | Glu | Lys | Glu 140 | Thr | Asp | Asn | Thr |
| Lys 145 | Pro | Asn | Arg | Met | Pro 150 | Val | Ala | Pro | Tyr | Trp 155 | Thr | Ser | Pro | Glu | Lys 160 |
| Met | Glu | Lys | Lys | Leu 165 | His | Ala | Val | Pro 170 | Ala | Ala | Lys | Thr | Val 175 | Lys | Phe |
| Lys | Cys | Pro | Ser 180 | Ser | Gly | Thr | Pro | Asn 185 | Pro | Thr | Leu | Arg | Trp 190 | Leu | Lys |
| Asn | Gly | Lys | Glu 195 | Phe | Lys | Pro | Asp | His 200 | Arg | Ile | Gly | Gly 205 | Tyr | Lys | Val |
| Arg | Tyr 210 | Ala | Thr | Trp | Ser | Ile 215 | Ile | Met | Asp | Ser | Val 220 | Val | Pro | Ser | Asp |
| Lys 225 | Gly | Asn | Tyr | Thr | Cys 230 | Ile | Val | Glu | Asn | Glu 235 | Tyr | Gly | Ser | Ile | Asn 240 |
| His | Thr | Tyr | Gln | Leu 245 | Asp | Val | Val | Glu | Arg 250 | Ser | Pro | His | Arg | Pro 255 | Ile |
| Leu | Gln | Ala | Gly 260 | Leu | Pro | Ala | Asn | Lys 265 | Thr | Val | Ala | Leu | Gly 270 | Ser | Asn |
| Val | Glu | Phe 275 | Met | Cys | Lys | Val | Tyr 280 | Ser | Asp | Pro | Gln | Pro 285 | His | Ile | Gln |
| Trp | Leu 290 | Lys | His | Ile | Glu | Val 295 | Asn | Gly | Ser | Lys | Ile 300 | Gly | Pro | Asp | Asn |
| Leu 305 | Pro | Tyr | Val | Gln | Ile 310 | Leu | Lys | Thr | Ala | Gly 315 | Val | Asn | Thr | Thr | Asp 320 |
| Lys | Glu | Met | Glu | Val 325 | Leu | His | Leu | Arg | Asn 330 | Val | Ser | Phe | Glu | Asp 335 | Ala |
| Gly | Glu | Tyr | Thr 340 | Cys | Leu | Ala | Gly | Asn 345 | Ser | Ile | Gly | Leu | Ser 350 | His | His |
| Ser | Ala | Trp | Leu 355 | Thr | Val | Leu | Glu | Ala 360 | Leu | Glu | Glu | Arg 365 | Pro | Ala | Val |
| Met | Thr 370 | Ser | Pro | Leu | Tyr | Leu 375 | Glu | Ile | Ile | Ile | Tyr 380 | Cys | Thr | Gly | Ala |
| Phe 385 | Leu | Ile | Ser | Cys | Met 390 | Val | Gly | Ser | Val | Ile 395 | Val | Tyr | Lys | Met | Lys 400 |
| Ser | Gly | Thr | Lys | Lys 405 | Ser | Asp | Phe | His | Ser 410 | Gln | Met | Ala | Val | His 415 | Lys |
| Leu | Ala | Lys | Ser 420 | Ile | Pro | Leu | Arg | Arg 425 | Gln | Val | Thr | Val | Ser 430 | Ala | Asp |
| Ser | Ser | Ala 435 | Ser | Met | Asn | Ser | Gly 440 | Val | Leu | Leu | Val | Arg 445 | Pro | Ser | Arg |
| Leu | Ser 450 | Ser | Ser | Gly | Thr | Pro 455 | Met | Leu | Ala | Gly | Val 460 | Ser | Glu | Tyr | Glu |
| Leu 465 | Pro | Glu | Asp | Pro | Arg 470 | Trp | Glu | Leu | Pro | Arg 475 | Asp | Arg | Leu | Val | Leu 480 |
| Gly | Lys | Pro | Leu | Gly 485 | Glu | Gly | Cys | Phe | Gly 490 | Gln | Val | Val | Leu | Ala | Glu 495 |

| | | | | | | | | | | | | | | |
|---|---|---|---|---|---|---|---|---|---|---|---|---|---|---|
| Ala | Ile | Gly | Leu 500 | Asp | Lys | Asp | Lys | Pro 505 | Asn | Arg | Val | Thr | Lys 510 | Val | Ala |
| Val | Lys | Met 515 | Leu | Lys | Ser | Asp | Ala 520 | Thr | Glu | Lys | Asp | Leu 525 | Ser | Asp | Leu |
| Ile | Ser 530 | Glu | Met | Glu | Met | Met 535 | Lys | Met | Ile | Gly | Lys 540 | His | Lys | Asn | Ile |
| Ile 545 | Asn | Leu | Leu | Gly | Ala 550 | Cys | Thr | Gln | Asp | Gly 555 | Pro | Leu | Tyr | Val | Ile 560 |
| Val | Glu | Tyr | Ala | Ser 565 | Lys | Gly | Asn | Leu | Arg 570 | Glu | Tyr | Leu | Gln | Ala 575 | Arg |
| Arg | Pro | Pro | Gly 580 | Leu | Glu | Tyr | Cys | Tyr 585 | Asn | Pro | Ser | His | Asn 590 | Pro | Glu |
| Glu | Gln | Leu 595 | Ser | Ser | Lys | Asp | Leu 600 | Val | Ser | Cys | Ala | Tyr 605 | Gln | Val | Ala |
| Gly | Gly 610 | Met | Glu | Tyr | Leu | Ala 615 | Ser | Lys | Lys | Cys | Ile 620 | His | Arg | Asp | Leu |
| Ala 625 | Ala | Arg | Asn | Val | Leu 630 | Val | Thr | Glu | Asp | Asn 635 | Val | Met | Lys | Ile | Ala 640 |
| Asp | Phe | Gly | Leu | Ala 645 | Arg | Asp | Ile | His | His 650 | Ile | Asp | Tyr | Tyr | Lys 655 | Lys |
| Thr | Thr | Asn | Gly 660 | Arg | Leu | Pro | Val | Lys 665 | Trp | Met | Ala | Pro | Glu 670 | Ala | Leu |
| Phe | Asp | Arg 675 | Ile | Tyr | Thr | His | Gln 680 | Ser | Asp | Val | Trp | Ser 685 | Phe | Gly | Val |
| Leu | Leu 690 | Trp | Glu | Ile | Phe | Thr 695 | Leu | Gly | Gly | Ser | Pro 700 | Tyr | Pro | Gly | Val |
| Pro 705 | Val | Glu | Glu | Leu | Phe 710 | Lys | Leu | Leu | Lys | Glu 715 | Gly | His | Arg | Met | Asp 720 |
| Lys | Pro | Ser | Asn | Cys 725 | Thr | Asn | Glu | Leu | Tyr 730 | Met | Met | Met | Arg | Asp 735 | Cys |
| Trp | His | Ala | Val 740 | Pro | Ser | Gln | Arg | Pro 745 | Thr | Phe | Lys | Gln | Leu 750 | Val | Glu |
| Asp | Leu | Asp 755 | Arg | Ile | Val | Ala | Leu 760 | Thr | Ser | Asn | Gln | Glu 765 | Tyr | Leu | Asp |
| Leu | Ser 770 | Met | Pro | Leu | Asp | Gln 775 | Tyr | Ser | Pro | Ser | Phe 780 | Pro | Asp | Thr | Arg |
| Ser 785 | Ser | Thr | Cys | Ser | Ser 790 | Gly | Glu | Asp | Ser | Val 795 | Phe | Ser | His | Glu | Pro 800 |
| Leu | Pro | Glu | Glu | Pro 805 | Ser | Leu | Pro | Arg | His 810 | Pro | Ala | Gln | Leu | Ala 815 | Asn |
| Arg | Gly | Leu | Lys 820 | Arg | Arg | | | | | | | | | | |